United States Patent [19]

Ishiguro et al.

[11] Patent Number: 4,485,169

[45] Date of Patent: Nov. 27, 1984

[54] SILVER HALIDE PHOTOGRAPHIC LIGHT-SENSITIVE MATERIALS

[75] Inventors: Shoji Ishiguro; Tetsuro Kojima; Akio Mitsui, all of Kanagawa, Japan

[73] Assignee: Fuji Photo Film Co., Ltd., Kanagawa, Japan

[21] Appl. No.: 473,307

[22] Filed: Mar. 8, 1983

[30] Foreign Application Priority Data

Mar. 8, 1982 [JP] Japan ................................. 57/36104

[51] Int. Cl.$^3$ ................................................ G03C 1/34
[52] U.S. Cl. .................................... 430/615; 430/600
[58] Field of Search ............................. 430/615, 600

[56] References Cited

U.S. PATENT DOCUMENTS 3,526,507  9/1970  Ishikawa et al. ..................... 430/615
4,241,164 12/1980  Mifune et al. ....................... 430/600

FOREIGN PATENT DOCUMENTS 39-10166  6/1964  Japan ................................. 430/615

Primary Examiner—Won H. Louie

Attorney, Agent, or Firm—Sughrue, Mion, Zinn, Macpeak, and Seas

[57] ABSTRACT

The fading of latent images in photographic films or the like containing at least a silver halide emulsion layer is greatly diminished by the addition of a compound of the general formulae

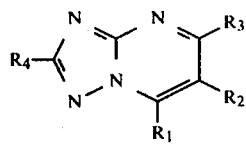

or

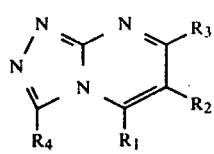

to the emulsion layer or another hydrophilic colloid layer. The substituents $R_1$ to $R_4$ are defined within.

15 Claims, No Drawings

SILVER HALIDE PHOTOGRAPHIC LIGHT-SENSITIVE MATERIALS

FIELD OF THE INVENTION

The present invention relates to silver halide photographic light-sensitive materials and, particularly, to silver halide photographic light-sensitive materials in which the fading of latent images is prevented.

BACKGROUND OF THE INVENTION

It is well known that two processes consisting of a photographing exposure process for forming latent images and a development process for converting the formed latent images into silver images or dye images are necessary in obtaining images by a silver halide photographic process (for example, refer to Mees and James, *The Theory of the Photographic Process*). The formation of latent images by photographic exposure is chemically caused by a very slight change of silver halide crystals, and latent images themselves are essentially unstable. Accordingly, the latent images have a propensity to easily decay over the passage of time from photographic exposure to development processing, which characteristic is known as the fading of latent images. The progress of the fading of the latent images generally depends upon the preservation condition of the exposed photographic materials. For example, it has been observed that the degree of fading is remarkably high when such materials are preserved at a high temperature, and is low when such are preserved at a low temperature.

The simplest process for avoiding the disadvantages due to the fading of latent images is obviously one which comprises carrying out development just after photographic exposure; and the second simplest process is one in which the photographic sensitive materials are preserved by cooling at a low temperature for the period from exposure to development. These processes are easy solutions from the chemical viewpoint, but it is hard to say that they are the preferred solutions, considering the users convenience. Noting the practical conditions of use and the practical state of such use, in the case of negative materials and reversal materials for photography, they are often allowed to stand at room temperature for several months from exposure to development. In the case of positive materials for copying, these are also allowed to sometimes stand for several months.

From the above-described reason, it is desired to obtain silver halide photographic light-sensitive materials in which the fading of latent images is prevented, and various methods have been attempted hitherto. However, as a result of our studies, it has been found that all of these known processes, namely, the process using hydroxyl group substituted aromatic compounds as described in German Pat. No. 1,107,508, the process using 1,3-diones as described in U.S. Pat. No. 3,447,926, the process using nitrilotriacetic acid as described in U.S. Pat. No. 3,318,702, the process described in U.S. Pat. No. 3,424,583 and the process described in German Pat. No. 1,173,339, are insufficient for the abovedescribed purpose.

SUMMARY OF THE INVENTION

As a result of various studies concerning the above, the present inventors have found that tetraazaindene compounds having certain substituents have the effect of preventing the fading of latent images.

Namely, the present invention relates to silver halide photographic light-sensitive materials comprising a base and at least a silver halide emulsion layer, wherein said emulsion layer or another hydrophilic colloid layer contains a compound represented by the following formulae (I) or (II):

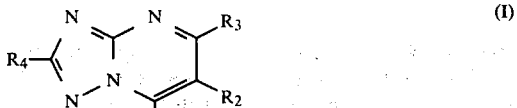

(I)

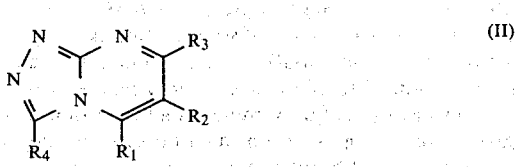

(II)

wherein $R_1$, $R_2$, $R_3$ and $R_4$ each represents a hydrogen atom, an alkyl group (preferably, an alkyl group having 1 to 10 carbon atoms which is substituted or not substituted, for example, a methyl group, an ethyl group, an n-propyl group, an isopropyl group, an n-butyl group, a t-butyl group, an n-octyl group, a methoxyethyl group, a hydroxyethyl group, a hydroxymethyl group or a phenoxymethyl group, etc.), an alkenyl group (preferably, an alkenyl group having 2 to 10 carbon atoms which is substituted or not substituted, for example, a vinyl group, an allyl group or a propargyl group, etc.), an aralkyl group (preferably, an aralkyl group having 7 to 12 carbon atoms which is substituted or not substituted, for example, a benzyl group or a phenethyl group, etc.), an aryl group (preferably, an aryl group having 6 to 12 carbon atoms which is substituted or not substituted, for example, a phenyl group, a 4-methylphenyl group or a 4-methoxyphenyl group, etc.), an alkylthio group (preferably, an alkylthio group having 1 to 10 carbon atoms which is substituted or not substituted, for example, a methylthio group or an ethylthio group, etc.), an arylthio group (preferably, an arylthio group having 6 to 12 carbon atoms which is substituted or not substituted, for example, a phenylthio group, etc.), a mercapto group, an alkoxy group (preferably, an alkoxy group having 1 to 10 carbon atoms which is substituted or not substituted, for example, a methoxy group, an ethoxy group, a methoxyethoxy group or a hydroxyethoxy group, etc.), an aryloxy group (preferably, an aryloxy group having 6 to 12 carbon atoms which is substituted or not substituted, for example, a phenoxy group or a 4-methylphenoxy group, etc.), a hydroxyl group, an alkylamino group (preferably, an alkylamino group having 1 to 10 carbon atoms which is substituted or not substituted, for example, a dimethylamino group, a methylamino group or a diethylamino group, etc.), an arylamino group (preferably, an arylamino group having 6 to 12 carbon atoms which is substituted or not substituted, for example, an anilino group, etc.), an amino group, a halogen atom (for example, a chlorine atom, a bromine atom or a fluorine atom, etc.), a cyano group, an alkoxycarbonyl group (preferably, an alkoxycarbonyl group of which alkoxy moiety has 1 to 10 carbon atoms which is substituted or not substituted, for example, an ethoxycarbonyl group, etc.),

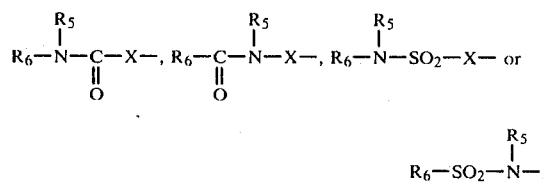

wherein X represents a bonding group represented by an alkylene group (preferably, an alkylene group having 1 to 5 carbon atoms which is substituted or not substituted, for example, a methylene group, a propylene group or a 2-hydroxypropylene group, etc.), and $R_5$ and $R_6$, which may be identical or different, each represents a hydrogen atom, an alkyl group (preferably, an alkyl group having 1 to 10 carbon atoms which is substituted or not substituted, for example, a methyl group, an ethyl group, an n-propyl group, an isopropyl group, an n-butyl group, a t-butyl group, an n-octyl group, a methoxyethyl group or a hydroxyethyl group, etc.), an alkenyl group (preferably, an alkenyl group having 2 to 10 carbon atoms which is substituted or not substituted, for example, an allyl group or a propargyl group, etc.), an aralkyl group (preferably, an aralkyl group having 7 to 12 carbon atoms which is substituted or not substituted, for example, a benzyl group, a phenethyl group or a vinylbenzyl group, etc.), an aryl group (preferably, an aryl group having 6 to 12 carbon atoms which is substituted or not substituted, for example, a phenyl group or a 4-methylphenyl group, etc.), or a heterocyclic group (for example, a 2-pyridyl group, etc.); but at least one of $R_1$, $R_2$, $R_3$ and $R_4$ is a hydroxyl group and at least one of the others is a group represented by

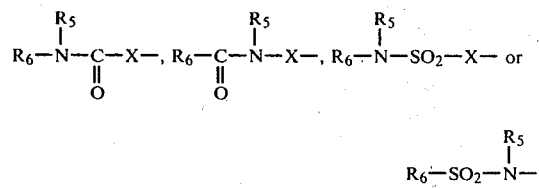

DETAILED DESCRIPTION OF THE PREFERRED EMBODIMENTS

In the general formulae (I) or (II) given above, it is more preferred that at least one of $R_1$ to $R_4$ is a group represented by

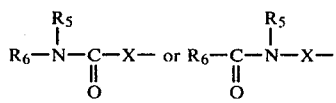

and, particularly, a group represented by

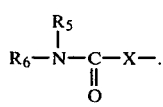

In the formulae, it is more preferred that $R_1$ be a hydroxyl group. Further, it is more preferred that $R_3$ be a group represented by

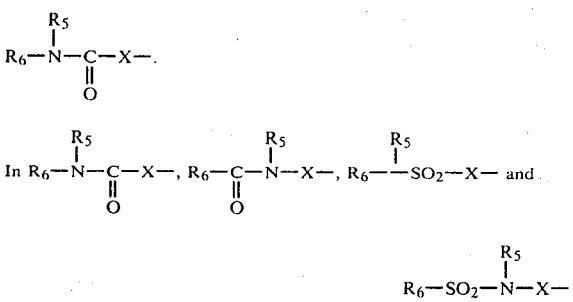

of $R_1$ to $R_4$, it is more preferred that X represent a methylene group, and $R_5$ and $R_6$, which may be identical or different from each other, be each an alkenyl group or an aralkyl group (particularly preferably an alkenyl group).

In the following, examples of tetraazaindenes represented by the general formulae (I) and (II) are described, but the compounds used in the present invention are not so limited.

| | |
|---|---|
| Compound 1 | 6-(N,N—Diallylcarbamoylmethyl)-4-hydroxy-1,3,3a,7-tetraazaindene |
| Compound 2 | 6-(N—Ethylcarbamoylethyl)-4-hydroxy-2-methyl-1,3,3a,7-tetraazaindene |
| Compound 3 | 6-(N—Phenylcarbamoylmethyl)-4-hydroxy-1,3,3a,7-tetraazaindene |
| Compound 4 | 6-(N—2-Pyridylcarbamoylmethyl)-4-hydroxy-1,3,3a,7-tetraazaindene |
| Compound 5 | 6-(N—Allylcarbamoylmethyl)-2-allyl-4-hydroxy-1,3,3a,7-tetraazaindene |
| Compound 6 | 6-(N—Allylcarbamoylmethyl)-4-hydroxy-1,3,3a,7-tetraazaindene |
| Compound 7 | 4-Hydroxy-2-methylthio-6-(N—vinylbenzylcarbamoylmethyl)-1,3,3a,7-tetraazaindene |
| Compound 8 | 4-Hydroxy-6-(N—vinylbenzylcarbamoylmethyl)-1,3,3a,7-tetraazaindene |
| Compound 9 | 6-(N,N—Diethylcarbamoylmethyl)-5-ethoxycarbonyl-4-hydroxy-1,3,3a,7-tetraazaindene |
| Compound 10 | 4-Hydroxy-6-(N—propylcarbamoylpropyl)-2-phenoxy-1,3,3a,7-tetraazaindene |
| Compound 11 | 6-(N—Benzylcarbamoylmethyl)-4-hydroxy-1,3,3a,7-tetraazaindene |
| Compound 12 | 5-Cyano-6-(N,N—diallylcarbamoylmethyl)-4-hydroxy-1,3,3a,7-tetraazaindene |
| Compound 13 | 4-Hydroxy-6-(N—octylcarbamoylmethyl)-2-phenyl-1,3,3a,7-tetraazaindene |
| Compound 14 | 6-(N—Benzylcarbamoylmethyl)-5-bromo-4-hydroxy-1,3,3a,7-tetraazaindene |
| Compound 15 | 2-Benzyl-6-(N,N—diethoxycarbamoylmethyl)-4-hydroxy-1,3,3a,7-tetraazaindene |
| Compound 16 | 6-(N—Allylcarbamoylmethyl)-4-hydroxy-2-dimethylamino-1,3,3a,7-tetraazaindene |
| Compound 17 | 6-(N—Benzylcarbamoylmethyl)-4-hydroxy-2-phenylthio-1,3,3a,7-tetraazaindene |
| Compound 18 | 4-Hydroxy-6-(N—methyl-N—phenylcarbamoylmethyl)-1,3,3a,7-tetraazaindene |
| Compound 19 | 4-Hydroxy-6-(N—propylcarbamoylmethyl)-1,3,3a,7-tetraazaindene |
| Compound 20 | 6-(N,N—Dipropylcarbamoylmethyl)-4-hydroxy-1,3,3a,7-tetraazaindene |
| Compound 21 | 6-(N—Benzyl-N—methylcarbamoylmethyl)-4-hydroxy-1,3,3a,7-tetraazaindene |
| Compound 22 | 6-[N—(2-methoxyphenyl)carbamoylmethyl]9 -4-hydroxy-1,3,3a,7-tetraazaindene |
| Compound 23 | 6-[N—(2-methylphenyl)carbamoylmethyl]-4-hydroxy-1,3,3a,7-tetraazaindene |
| Compound 24 | 6-[N—(2,5-dimethoxyphenyl)carbamoylmethyl]-4-hydroxy-1,3,3a,7-tetraazaindene |
| Compound 25 | 6-Acetylaminomethyl-4-hydroxy-1,3,3a,7-tetraazaindene |
| Compound 26 | 6-(3-Butenoylaminomethyl)-4-hydroxy-1,3,3a,7-tetraazaindene |
| Compound 27 | 4-Hydroxy-6-(α-phenylacetylaminomethyl)-1,3,3a,7-tetraazaindene |

-continued

| | |
|---|---|
| Compound 28 | 6-(N,N—Diallylsulfamoylmethyl)-4-hydroxy-1,3,3a,7-tetraazaindene |
| Compound 29 | 6-(N—Benzylsulfamoylmethyl)-4-hydroxy-1,3,3a,7-tetraazaindene |
| Compound 30 | 4-Hydroxy-6-(methanesulfonamidomethyl)-1,3,3a,7-tetraazaindene |
| Compound 31 | 6-Benzenesulfonamidomethyl-4-hydroxy-1,3,3a,7-tetraazaindene |
| Compound 32 | 6-(N,N—Diallylcarbamoylmethyl)-4-hydroxy-1,2,3a,7-tetraazaindene |
| Compound 33 | 6-(N—Vinylbenzylcarbamoylmethyl)-4-hydroxy-1,2,3a,7-tetraazaindene |
| Compound 34 | 6-Acetylaminomethyl-4-hydroxy-1,2,3a,7-tetraazaindene |
| Compound 35 | 6-(3-Butenoylaminomethyl)-4-hydroxy-1,2,3a,7-tetraazaindene |
| Compound 36 | 6-Benzenesulfonamidomethyl-4-hydroxy-1,2,3a,7-tetraazaindene |
| Compound 37 | 6-(N—Allylsulfamoyl)-4-hydroxy-1,2,3a,7-tetraazaindene |

Particularly preferred compounds are Compounds 7, 8 and 12.

General processes for synthesizing tetraazaindenes represented by the general formula (I) and (II) have been described in *Ber.*, 42, 4638 (1909) and *Photo-Rundsch*, 26, 414, 437 and 465 (1961), etc. In the following, examples of the synthesis of typical compounds are described, but other tetraazaindenes can be easily synthesized according to such examples.

SYNTHESIS EXAMPLE 1

Synthesis of 6-(N,N-Diallylcarbamoylmethyl)-4-hydroxy-1,3,3a,7-tetraazaindene (Compound 1)

126 g of aminotriazole, 304 g of diethyl acetonedicarboxylate and 60 ml of acetic acid were refluxed with heating for 8 hours. After cooling in the air, 500 ml of ethyl acetate was added to precipitate white crystals. The resulting crystals were filtered out and washed with ethyl acetate to obtain 305 g of 6-ethoxycarbonylmethyl-4-hydroxy-1,3,3a,7-tetraazaindene. Then, 300 g of the resulting crystals, 130 g of sodium hydroxide and 500 ml of water were heated to 80° C. for 3 hours. After the reaction, 340 ml of concentrated hydrochloric acid was slowly added to precipitate white crystals. The resulting crystals were filtered out and recrystallized from water to obtain 212 g of 6-carboxymethyl-4-hydroxy-1,3,3a,7-tetraazaindene.

143 g of the resulting crystals and 72 g of diallylamine were dissolved in 1.5 l of dimethylformamide with stirring at room temperature. To this solution, 152 g of N,N-dicyclohexylcarbodiimide was added dropwise. After this addition, the mixture was stirred at room temperature for 8 hours to separate white crystals (N,N-dicyclohexylurea). After the separated crystals were filtered off, the filtrate was poured into 3 l of water to separate white crystals. The separated crystals were filtered out and recrystallized from acetonitrile to obtain 171 g of the desired 6-(N,N-diallylcarbamoylmethyl)-4-hydroxy-1,3,3a,7-tetraazaindene.

The product was identified by the results of IR, NMR and elementary analysis.

Elementary Analysis ($C_{13}H_{15}N_5O_2$) Theoretical Value (%): H: 5.53 C: 57.13 N: 25.62. Measured Value (%): H: 5.48 C: 57.23 N: 25.58.

SYNTHESIS EXAMPLE 2

Synthesis of 4-hydroxy-6-(N-vinylbenzylcarbamoylmethyl)-1,3,3a,7-tetraazaindene (Compound 8)

143 g of 6-carboxymethyl-4-hydroxy-1,3,3a,7-tetraazaindene prepared in Synthesis Example 1 and 98 g of vinylbenzylamine were dissolved in 1 l of dimethylformamide with stirring at room temperature. To the solution, 152 g of N,N-dicyclohexylcarbodiimide was added dropwise. After addition, the mixture was stirred at room temperature for 6 hours to separate white crystals (N,N-dicyclohexylurea). After the reaction, the separated crystals were filtered off and the filtrate was poured into 2 l of water to separate white crystals. The separated crystals were filtered out and recrystallized from acetonitrile to obtain 180 g of the desired 4-hydroxy-6-(N-vinylbenzylcarbamoylmethyl)-1,3,3a,7-tetraazaindene.

The product was identified by the results of IR, NMR and elementary analysis.

Elementary Analysis ($C_{16}H_{15}N_5O_2$) Theoretical Value (%): H: 4.89 C: 62.13 N: 22.64. Measured Value (%): H: 4.84 C: 62.10 N: 22.59.

The tetraazaindene compounds of the present invention can be contained in a suitable silver halide emulsion layer or another hydrophilic colloid layer of the photographic light-sensitive material. That is, they may be added to photographic silver halide emulsion layers or may be incorporated into other light-insensitive layers, for example, a protective layer, an intermediate layer, a filter layer or an antihalation layer, etc. Preferably, they are added to silver halide photographic emulsion layers.

It is preferred that the tetraazaindene compounds be used in an amount of $1 \times 10^{-5}$ to 1 mol per mol of silver halide and, preferably, $2 \times 10^{-4}$ to $5 \times 10^{-2}$ mol.

It is not necessary to particularly restrict the time of adding the compounds of the present invention, but it is preferred to add the same after chemical ageing or just before coating, because both the effect of preventing the fading of latent images and the effect of stabilizing the silver halide photographic light-sensitive emulsions are remarkably exhibited.

In order to add the compounds of the present invention to the photographic light-sensitive materials, it is possible to use conventional methods for adding additives to photographic emulsions. For example, water-soluble compounds are added to the emulsions as an aqueous solution having a suitable concentration and water-insoluble or poorly soluble compounds are added as a solution resulting from dissolving the same in a suitable organic solvent which does not have an adverse influence upon photographic properties, selected from, for example, alcohols, ethers, glycols, ketones, esters and amides, etc. It is also possible to use well known methods for adding water-insoluble couplers (the so-called oil-soluble couplers) as a state of dispersion to the emulsion.

The silver halide particles used in the present invention may be either the substantially surface latent image type or the substantially internal latent image type. Substantially surface latent image type silver halide particles are effectively used.

The term "substantially surface latent image type" as used in the present invention is defined as where the sensitivity obtained by surface development (A) is higher than that obtained by internal development (B)

when a light-sensitive material prepared by applying an emulsion, to which the compound represented by the general formulae (I) or (II) of the present invention is not added, to a conventionally used transparent base is exposed to light for 1 to 1/100 second and thereafter developed by the following surface development (A) and internal development (B). Here, the sensitivity is defined as the following.

$$S = (100/Eh)$$

where S represents a sensitivity and Eh represents an exposure necessary to obtain the middle density between the maximum density ($D_{max}$) and the minimum density ($D_{min}$): $\frac{1}{2}(D_{max}+D_{min})$.

Surface Development (A)

Development is carried out in a developing solution having the following composition at a temperature of 20° C. for 10 minutes.

| | |
|---|---|
| N—Methyl-p-aminophenol (hemisulfate) | 2.5 g |
| Ascorbic acid | 10.0 g |
| Sodium metaborate tetrahydrate | 35.0 g |
| Potassium bromide | 1.0 g |
| Water to make | 1 l |

Internal Development (B)

The light-sensitive material is treated in a bleaching solution containing 3 g/l of red prussiate and 0.0125 g/l of phenosafranine at about 20° C. for 10 minutes, followed by washing with water for 10 minutes and developing in a developing solution having the following composition at 20° C. for 10 minutes.

| | |
|---|---|
| N—Methyl-p-aminophenol (hemisulfate) | 2.5 g |
| Ascorbic acid | 10.0 g |
| Sodium metaborate tetrahydrate | 35.0 g |
| Potassium bromide | 1.0 g |
| Sodium thiosulfate | 3.0 g |
| Water to make | 1 l |

The silver halide in the silver halide light-sensitive materials used in the present invention is composed of silver chloride, silver chlorobromide, silver bromide, silver iodobromide or silver iodobromochloride. The average particle size of silver halide particles is not particularly restricted, but it is preferred that they not be larger than 3μ.

Although the so-called primitive emulsions which are not subjected to chemical sensitization can be used, silver halide emulsions generally are subjected to chemical sensitization. In order to carry out chemical sensitization, it is possible to use methods described in P. Glafkides, *Chimie et Physique Photographique* (Paul Montel, 1967), V. L. Zelikman et al., *Making and Coating Photographic Emulsion* (The Focal Press, 1964), and *Die Grundlagen der Photographischen Prozesse mit Silberhalogeniden*, edited by H. Frieser (Akademische Verlagsgesellschaft, 1968).

Namely, it is possible to use a sulfur sensitization process using thiosulfates, thioureas, thiazoles, rhodanines or activated gelatin; a reduction sensitization process using stannous salts, amines, hydrazines, formamidinesulfinic acid or silane compounds, etc.; and a noble metal sensitization process using gold complex salts or complex salts of other metals belonging to Group VII in the Periodic Table such as platinum, iridium or palladium, etc.; which may be used alone or in combination.

In order to increase the sensitivity, improve contrast or accelerate development, it is possible to add polyalkylene oxides and derivatives thereof such as ethers, esters or amines; etc., thioether compounds, thiomorpholines, quaternary ammonium salt compounds, urethane derivatives, urea derivatives, imidazole derivatives and 3-pyrazolidones, etc. For example, it is possible to use those described in U.S. Pat. Nos. 2,400,532, 2,423,549, 2,716,062, 3,617,280, 3,772,021 and 3,808,003, and others.

In order to prevent fogging or stabilize photographic properties in the step of producing the light-sensitive materials, during preservation or during photographic processing, it is possible to add various compounds. Namely, it is possible to add many compounds known as antifoggants or stabilizers, such as azoles, for example, benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles and mercaptotetrazoles (particularly, 1-phenyl-5-mercaptotetrazole), etc.; mercaptopyrimidines; mercaptotriazines; thioketo compounds, for example, oxazolinethione; triazaindenes, 4-hydroxy-6-methyl-(1,3,3a,7)-tetraazaindene and pentaazaindenes, etc.; and benzenesulfinic acid and benzenesulfonic acid amides, etc.

In the present invention, gelatin is advantageously used as a binder or as a protective colloid for the photographic emulsions, but other hydrophilic colloids can be used as well.

For example, it is possible to use proteins such as gelatin derivatives, graft polymers of gelatin and other high polymers, albumin or casein, etc.; saccharide derivatives such as cellulose derivatives such as hydroxyethyl cellulose, carboxymethyl cellulose or cellulose sulfuric acid ester, etc., sodium alginate or starch derivatives, etc.; and various synthetic hydrophilic high molecular substances such as homo- or copolymers such as polyvinyl alcohol, polyvinyl alcohol partial acetal, poly-N-vinylpyrrolidone, polyacrylic acid, polymethacrylic acid, polyacrylamide, polyvinylimidazole or polyvinylpyrazole, etc.

As gelatin, not only lime treated gelatin but acid treated gelatin may be used, and gelatin hydrolyzed products and gelatin enzymic decomposition products can be used as well.

The photographic emulsion layers or other hydrophilic colloid layers in the light-sensitive materials of the present invention may contain various known surface active agents for use as coating assistants or for various purposes such as for preventing static charges, improvement of lubricating properties, emulsification and dispersion, prevention of adhesion or improvement of photographic properties (for example, acceleration of development, hard tone, and sensitization), etc.

For example, it is possible to use nonionic surface active agents such as saponin, alkylene oxide derivatives (for example, polyethylene glycols, polyalkylene glycol alkylamine or amides and polyethylene oxide addition products of silicone, etc.), glycidol derivatives (for example, alkenylsuccinic acid polyglyceride, etc.), aliphatic acid esters of polyhydric alcohols, alkyl esters of saccharose, and urethanes or ethers of saccharose, etc.; anionic surface active agents such as triterpenoid saponin, alkyl carboxylic acid salts, alkylbenzenesulfonic acid salts, alkyl sulfuric acid esters, alkyl phosphoric acid esters, N-acyl-N-alkyltaurines, sulfosuccinic acid esters or sulfoalkyl polyoxyethylene alkylphenyl ethers, etc.; ampholytic surface active agents such as amino acids, aminoalkylsulfonic acids, aminoalkylsulfuric or phosphoric acid esters, alkylbetaines, amine imides or amine oxides, etc.; and cationic surface active agents such as alkylamine salts, aliphatic or aromatic quaternary ammonium salts, heterocyclic quaternary ammonium salts such as pyridinium or imidazolium salts, or aliphatic or heterocyclic phosphonium or sulfonium salts, etc.

In the photographic light-sensitive materials of the present invention, the photographic emulsion layers and other hydrophilic colloid layers may contain a dispersion of water-insoluble or poorly soluble synthetic polymers for the purpose of improving dimensional stability. For example, it is possible to use polymers composed of one or more of alkyl acrylates or methacrylates, alkoxyalkyl acrylates or methacrylates, glycidyl acrylates or methacrylates, acryl or methacrylamide, vinyl esters (for example, vinyl acetate), acrylonitrile, olefins and styrene, etc., and polymers composed of the above-described monomer and acrylic acid, methacrylic acid, $\alpha,\beta$-unsaturated dicarboxylic acid, hydroxyalkyl acrylate or methacrylate, sulfoalkyl acrylate or methacrylate or styrene sulfonic acid, etc., as a monomer component.

In the photographic light-sensitive materials of the present invention, the photographic emulsion layers and other hydrophilic colloid layers may contain inorganic or organic hardening agents. For example, it is possible to use chromium salts (chromium alum or chromium acetate, etc.), aldehydes (formaldehyde, glyoxal or glutaraldehyde, etc.), N-methylol compounds (dimethylolurea or methyloldimethylhydantoin, etc.), dioxane derivatives (2,3-dihydroxydioxane, etc.), active vinyl compounds (1,3,5-triacryloyl-hexahydro-s-triazine or bis(vinylsulfonyl)methyl ether, etc.), active halogen compounds (2,4-dichloro-6-hydroxy-s-triazine, etc.), mucohalogenic acids (mucochloric acid or mucophenoxychloric acid, etc.), isoxazoles, dialdehyde starch, and 2-chloro-6-hydroxytriazinyl gelatin, etc., which may be used alone or in combination.

The photographic emulsions of the present invention may be spectrally sensitized with methine dyes or others. Examples of dyes used include cyanine dyes, merocyanine dyes, compound cyanine dyes, compound merocyanine dyes, holopolar cyanine dyes, hemicyanine dyes, styryl dyes and hemioxonol dyes. Particularly useful dyes are those belonging to merocyanine dyes and compound merocyanine dyes. In these dyes, any nucleus conventionally used for cyanine dyes can be utilized as a basic heterocyclic nucleus. Namely, it is possible to utilize a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus and a pyridine nucleus, etc.; the above-described nuclei with which an alicyclic hydrocarbon ring fuses; the above-described nuclei with which an aromatic hydrocarbon ring fuses, namely, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus, etc. These nuclei may have substituents on carbon atoms.

In the merocyanine dyes and compound merocyanine dyes, it is possible to utilize, as nuclei having a ketomethylene structure, 5 to 6 member heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus or a thiobarbituric acid nucleus, etc.

In the photographic light-sensitive materials of the present invention, the hydrophilic colloid layers may contain water-soluble dyes (oxonol dyes, hemioxonol dyes, styryl dyes, merocyanine dyes, cyanine dyes and azo dyes, etc.) as filter dyes or for other purposes such as preventing irradiation.

The photographic emulsions of the present invention may contain dye image forming couplers, namely, compounds which form a dye by reacting with an oxidation product of aromatic amine (generally, primary amine) developing agents (hereinafter referred to as couplers). The couplers are desired to have a hydrophobic group called a ballast group in the molecule by which they become non-diffusible. The couplers may be any of 4-equivalent ones and 2-equivalent ones to silver ions. Further, colored couplers having an effect of color correction or couplers which release a development inhibitor (the so-called DIR coupler) may be contained therein. The couplers may be ones which form a colorless product by a coupling reaction.

As yellow couplers, known opened chain ketomethylene couplers can be used. Among them, benzoylacetanilide compounds and pivaloylacetanilide compounds are advantageously used.

As magenta couplers, pyrazolone compounds, imidazolone compounds, and cyanoacetyl compounds can be used, and particularly, pyrazolone compounds are advantageously used.

As cyan couplers, phenol compounds and naphthol compounds, etc., can be used.

As DIR couplers, it is possible to use those described in, for example, U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454 and Japanese Patent Application (OPI) No. 69624/77 (the term "OPI" as used herein refers to a "published unexamined Japanese patent application").

In addition to DIR couplers, compounds which release a development inhibitor by development may be contained in the light-sensitive materials. For example, it is possible to use those described in U.S. Pat. Nos. 3,297,445 and 3,379,529 and German Patent Application (OLS) No. 2,417,914.

Two or more of the above-described couplers may be contained in the same layer. The same compound may be contained in two or more different layers.

Light-sensitive materials produced by the present invention may contain hydroquinone derivatives, aminophenol derivatives, gallic acid derivatives and ascorbic acid derivatives, etc., as anti-color-fogging agents.

In the light-sensitive materials produced by the present invention, the hydrophilic colloid layers may contain ultraviolet ray absorbing agents such as benzotriazole compounds substituted by an aryl group.

The photographic emulsions of the present invention are applied to a flexible base such as a conventionally used plastic film (cellulose nitrate, cellulose acetate or polyethylene terephthalate, etc.) or paper, etc., or a rigid base such as glass, etc.

The present invention can be applied to multilayer multicolor photographic materials having at least two layers each having a different sensitivity. Multilayer natural color photographic materials each generally has at least a red-sensitive emulsion layer, a green-sensitive emulsion layer and a blue-sensitive emulsion layer on a base. The order of these layers is suitably determined as occasion demands. Generally, the red-sensitive emulsion layer contains a cyan coupler, the green-sensitive emulsion layer contains a magenta coupler, and the blue-sensitive emulsion layer contains a yellow coupler, but, if desired, other combinations may be utilized.

Exposure for obtaining photographic images in the present invention is suitably carried out by a conventional method. Namely, it is possible to use any of various known light sources, for example, natural light (sunlight), tungsten lamps, fluorescent lamps, mercury lamps, xenon arc lamps, carbon arc lamps, xenon flash lamps and cathode ray tube flying spots. As the exposure time, it is possible to use not only exposures in a range from 1/1,000 second to 1 second as is used in conventional cameras, but also exposures shorter than 1/1,000 second, for example, $1 \times 10^{-4}$ to $1 \times 10^{-6}$ second using a xenon flash lamp or a cathode ray tube, and exposures longer than 1 second.

In order to carry out photographic processing of the light-sensitive materials of the present invention, any known process can be used. As processing solutions, known ones can be used. The processing temperature is selected generally in the range of 18° C. to 50° C., but a temperature lower than 18° C. or a temperature higher than 50° C. may be used. Any development processing for forming silver images (black-and-white photographic processing) and color photographic processing comprising development processing for forming dye images can be adopted according to the purpose.

The developing solution used when carrying out black-and-white photographic processing may contain known developing agents. As developing agents, it is possible to use dihydroxybenzenes (for example, hydroquinone), 3-pyrazolidones (for example, 1-phenyl-3-pyrazolidone), aminophenols (for example, N-methyl-p-aminophenol), 1-phenyl-3-pyrazolines, ascorbic acid, and heterocyclic compounds such as a compound in which a 1,2,3,4-tetrahydroquinoline ring is fused with an indolene ring as described in U.S. Pat. No. 4,067,872, which agents may be used alone or in combination. The developing solution generally may further contain known preservatives, alkali agents, pH buffer agents and antifoggants, etc., and, if desired, dissolution assistants, color toning agents, development accelerators, surface active agents, defoaming agents, water softeners, hardeners and viscosity increasing agents, etc.

As the fixing solution, it is possible to use conventionally used compositions. As the fixing agent, it is possible to use not only thiosulfates and thiocyanates but also known organic sulfur compounds having a fixing effect. The fixing solution may contain watersoluble aluminum salts as a hardening agent.

In the case of forming dye images, conventional processes can be applied. A negative-positive process (described in, for example, *Journal of the Society of Motion Picture and Television Engineers, Vol.* 61, pages 667–701 (1953)), a color reversal process which comprises developing with a developing solution containing a black-and-white developing agent to form negative silver images, carrying out at least one uniform exposure or suitable fogging treatment, and subsequently carrying out color development to obtain dye positive images, and a silver dye bleaching process which comprises developing photographic emulsion layers containing dyes after exposure to form silver images, and bleaching dyes by utilizing the silver images as a bleaching catalyst, etc., may be used.

The color developing solution generally consists of an aqueous alkaline solution containing a color developing agent. As color developing agents, it is possible to use known primary aromatic amine developing agents, for example, phenylenediamines (for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline and 4-amino-3-methyl-N-ethyl-N-β-methoxyethylaniline, etc.).

In addition, those agents described in L. F. A. Mason, *Photographic Processing Chemistry*, pages 226–229 (issued by Focal Press, 1966), U.S. Pat. Nos. 2,193,015 and 2,592,364 and Japanese Patent Application (OPI) No. 64933/73, etc., may be used.

The color developing solution can further contain pH buffer agents such as sulfites, carbonates, borates and phosphates of alkali metals, and development inhibitors or antifogging agents such as bromides, iodides or organic antifoggants. If desired, it may contain water hardeners, preservatives such as hydroxylamine, organic solvents such as benzyl alcohol or diethylene glycol, development accelerators such as polyethylene glycol, quaternary ammonium salts or amines, color forming couplers, competitive couplers, fogging agents such as sodium borohydride, auxiliary developing agents such as 1-phenyl-3-pyrazolidone, viscosity increasing agents, polycarboxylic acid chelating agents as described in U.S. Pat. No. 4,083,723, and antioxidants as described in German Patent Application (OLS) No. 2,622,950, etc.

The photographic emulsion layers after color development are generally subjected to bleaching. The bleaching process may be carried out simultaneously with fixation or may be carried out separately. As bleaching agents, compounds of polyvalent metal such as iron (III), cobalt (III), chromium (VI) or copper (II), etc., peracids, quinones and nitroso compounds, etc., may be used. For example, it is possible to use ferricyanides; bichromates; organic complex salts of iron (III) or cobalt (III) with aminopolycarboxylic acids such as ethylenediaminetetraacetic acid, nitrilotriacetic acid or 1,3-diamino-2-propanoltetraacetic acid, etc., or organic acids such as citric acid, tartaric acid or malic acid, etc.; persulfates, permanganates; and nitrosophenol, etc. Among them, potassium ferricyanide, sodium ethylenediaminetetraacetato iron (III) complex and ammonium ethylenediaminetetraacetato iron (III) complex are particularly useful. Ethylenediaminetetraacetato iron (III) complexes are useful in both an independent bleaching solution and in a one-bath bleach-fixing solution.

To the bleaching solution or the bleach-fixing solution, it is possible to add various additives including bleach accelerators as described in U.S. Pat. Nos. 3,042,520 and 3,241,966 and Japanese Patent Publications Nos. 8506/70 and 8836/70, etc., and thiol compounds as described in Japanese Patent Application (OPI) No. 65732/78.

The photographic light-sensitive materials of the present invention are particularly suitable for use as photographing light-sensitive materials (for example, black-and-white negative films, color negative films and reversal films, etc.), because the fading of the latent images is not only remarkably prevented but also stabilized by using tetraazaindenes; but these materials may also be used for other uses (for example, black-and-white printing paper or color printing paper, etc.).

In the following, the present invention will be illustrated in greater detail with reference to examples thereof.

EXAMPLE 1

To a silver iodobromide gelatin emulsion containing 6% by mol of silver iodide (particle size: about 0.75μ), Relative sensitivities in the case of development just after exposure, in the case of development after being allowed to stand for 21 days at room temperature (20° to 25° C.) after exposure, and in the case of carrying out exposure and development after being preserved at a temperature of 50° C. under an atmosphere having a relative humidity of 20% for 7 days, are respectively shown in Table 1. By comparing these values, it is possible to ascertain the degree of fading of the latent images.

In Table 1, the relative sensitivity is a relative value of the reciprocal of an exposure at which the density 0.2 excluding fog density is obtained, based on the value of Sample No. 1 in the case of development just after exposure being equal to 100.

TABLE 1

| Sample No. | Compound | Amount mol/mol-Ag | Relative Sensitivity in the Case of Development just after Exposure | Relative Sensitivity in the Case of Development after Standing at Room Temperature for 21 Days after Exposure | Relative Sensitivity and Fog in the Case of Carrying out Exposure and Development after Standing at 50° C. and 20% RH for 7 Days | |
|---|---|---|---|---|---|---|
| | | | | | Relative Sensitivity | Fog |
| 1 | No addition | — | 100 | 83 | 115 | 0.13 |
| 2 | Compound 8 | $1.0 \times 10^{-3}$ | 100 | 91 | 115 | 0.06 |
| 3 | " | $4.5 \times 10^{-3}$ | 95 | 100 | 100 | 0.05 |
| 4 | " | $3.6 \times 10^{-3}$ | 100 | 93 | 115 | 0.06 |
| 5 | " | $1.1 \times 10^{-2}$ | 93 | 96 | 115 | 0.05 |
| 6 | Compound 22 | $9.0 \times 10^{-3}$ | 96 | 96 | 115 | 0.05 |
| 7 | Compound 23 | $4.2 \times 10^{-3}$ | 100 | 96 | 110 | 0.06 |
| 8 | " | $1.7 \times 10^{-2}$ | 100 | 96 | 103 | 0.05 |
| 9 | " | $5.1 \times 10^{-2}$ | 100 | 100 | 98 | 0.04 |
| 10 | Compound 24 | $4.2 \times 10^{-3}$ | 93 | 93 | 96 | 0.06 |
| 11 | " | $1.7 \times 10^{-2}$ | 91 | 96 | 89 | 0.05 |
| 12 | " | $5.1 \times 10^{-2}$ | 85 | 102 | 85 | 0.04 |
| 13 | Compound 4 | $5.1 \times 10^{-2}$ | 100 | 102 | 115 | 0.04 |
| 14 | Comparative* Compound A | $4.5 \times 10^{-4}$ | 100 | 83 | 115 | 0.07 |
| 15 | comparative* Compound A | $5.4 \times 10^{-3}$ | 100 | 83 | 100 | 0.06 |

*Comparative Compound A:

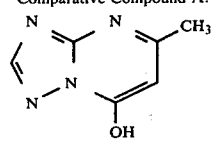

5 mg of sodium thiosulfate, 3.5 mg of potassium chloroaurate and 0.18 g of ammonium thiocyanate, based on 1 mol of silver halide, were added, and the emulsion was aged at 60° C. for 50 minutes.

This emulsion was divided into 15 parts, to which a compound of the present invention or a comparative compound as shown in the following Table 1, a hardening agent (sodium 2,4-dichloro-6-hydroxy-1,3,5-triazine) and a coating assistant (sodium dodecylbenzenesulfonate) were added. The emulsions were applied to a triacetate film, followed by drying to obtain samples.

These samples were exposed to light for 1/100 second through an optical wedge. After they were developed with a Kodak D-72 developing solution at 20° C. for 4 minutes, they were subjected to fixation, water wash and drying by conventional methods.

| D-72 Developing Solution: | |
|---|---|
| Metol | 3.1 g |
| Na₂SO₃ | 45.0 g |
| Hydroquinone | 12.0 g |
| Na₂CO₃ | 79.0 g |
| KBr | 1.9 g |
| Water to make | 1 l |

It will be understood from Table 1 that the fading of latent images is restrained by the addition of the compounds of the present invention (Sample Nos. 2 to 13). Further, it will be understood that an increase of fogging is restrained in the case where the samples are allowed to stand at a high temperature and low humidity.

EXAMPLE 2

To a paper base, both faces of which were laminated with polyethylene, the following first layer (lowest layer) to sixth layer (top layer) were applied to produce a multilayered color light-sensitive material (Sample 1). (In the table, mg/m² indicates the amount of application.)

| Sixth Layer (protective layer) | Gelatin | 1,500 mg/m² |
|---|---|---|
| Fifth Layer (red-sensitive layer) | Silver chlorobromide emulsion (silver bromide: 50% by mol, silver: 250 mg/m²) | |
| | Gelatin | 1,500 mg/m² |
| | Cyan coupler (*1) | 500 mg/m² |
| | Solvent for coupler (*2) | 250 mg/m² |
| Fourth Layer | Gelatin | 1,200 mg/m² |

| | | |
|---|---|---|
| (ultraviolet ray absorbing layer) | Ultraviolet ray absorbing agent (*3) | 700 mg/m² |
| | Solvent for ultraviolet ray absorbing agent (*2) | 250 mg/m² |
| Third Layer (green-sensitive layer) | Silver chlorobromide emulsion (silver bromide: 70% by mol, silver: 350 mg/m²) | |
| | Gelatin | 1,500 mg/m² |
| | Magenta coupler (*4) | 400 mg/m² |
| | Solvent for coupler (*5) | 400 mg/m² |
| Second Layer (intermediate layer) | Gelatin | 1,000 mg/m² |
| First Layer (blue-sensitive layer) | Silver chlorobromide (silver bromide: 80% by mol, silver: 350 mg/m²) | |
| | Gelatin | 1,500 mg/m² |
| | Yellow coupler (*6) | 500 mg/m² |
| | Solvent for coupler (*2) | 500 mg/m² |
| Base | Polyethylene laminated paper (polyethylene of the first layer side contains white pigment (TiO₂, etc.) and blue pigment (ultramarine, etc.)) | |

(*1) Cyan coupler: 2-[α-(2,4-Di-t-amylphenoxy)-butanamide]-4,6-dichloro-5-methylphenol
(*2) Solvent: Trinonyl phosphate
(*3) Ultraviolet ray absorbing agent: 2-(2-Hydroxy-3-sec-butyl-t-butylphenyl)benzo-triazole
(*4) Magenta coupler: 1-(2,4,6-Trichlorophenyl)-3-(2-chloro-5-tetradecanamide)-anilino-2-pyrazolin-5-one
(*5) Solvent for coupler: o-Cresyl phosphate
(*6) Yellow coupler: α-Pivaloyl-α-(2,4-dioxo-5,5-dimethyloxazolidin-3-yl)-2-chloro-5-[α-(2,4-di-t-amyl-phenoxy)butanamide]acetanilide To the third layer in Sample 1, Compound No. 8 of the present invention was added in an amount of $1 \times 10^{-2}$ mol/mol of Ag to produce Sample 2, and Compounds No. 6 and No. 1 were added in an amount of $1 \times 10^{-2}$ mol/mol of Ag to produce Samples 3 and 4, respectively. For comparison, Sample 5 was produced using Compound A.

The above-described light-sensitive materials were processed in the following steps immediately after exposure to green light through an optical wedge, or after being preserved in a dark box at room temperature for 2 days after exposure to green light through an optical wedge.

| Processing Step (33° C.) | |
|---|---|
| Color development | 3 minutes and 30 seconds |
| Bleach-fixation | 1 minute and 30 seconds |
| Water wash | 3 minutes |
| Drying (50 to 80° C.) | 2 minutes |

Compositions of each processing solution are as follows:

| Color Developing Solution: | |
|---|---|
| Benzyl alcohol | 12 ml |
| Diethylene glycol | 5 ml |
| Potassium carbonate | 25 g |
| Sodium chloride | 0.1 g |
| Sodium bromide | 0.5 g |
| Anhydrous sodium sulfite | 2 g |
| Hydroxylamine sulfate | 2 g |
| Fluorescent whitening agent | 1 g |
| N—Ethyl-N—β-methanesulfonamidoethyl-3-methyl-4-aminoaniline sulfate | 4 g |
| Water was added to make 1 liter, and | |

| Color Developing Solution: |
|---|
| NaOH was added to make the pH 10.2. |

| Bleach-Fixing Solution: | |
|---|---|
| Ammonium thiosulfate | 124.5 g |
| Sodium metabisulfite | 13.3 g |
| Anhydrous sodium sulfite | 2.7 g |
| EDTA ferric ammonium salt | 65 g |
| Color developing solution (described above) | 100 ml |
| pH was adjusted to 6.7 to 6.8 | |
| Water to make | 1 l |

The processing solutions used were those used for developing by means of a conventional roller transport type developing apparatus carrying out normal supplement, the composition of which reaches nearly to equilibrium.

The densities of the thus-resulting Samples 1 to 5 were measured by means of a Fuji automatic densitometer, and the results are shown in Table 2.

TABLE 2

| Sample No. | Compound | Sensitivity of GL Layer Processed just after Exposure | Density after 2 Days in the Case where Density $D_G$ in the Case of Processing just after Exposure Is 1.0 |
|---|---|---|---|
| 1 | No addition | 100 | 0.71 |
| 2 (present invention) | Compound 8 | 99 | 1.00 |
| 3 (present invention) | Compound 6 | 98 | 0.98 |
| 4 (present invention) | Compound 1 | 99 | 0.97 |
| 5 | Comparative* Compound A | 102 | 0.93 |

*Comparative Compound A:

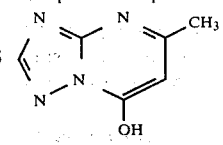

As is obvious from Table 2, in Samples 2, 3 and 4 using Compounds 8, 6 and 1 of the present invention, the sensitivity hardly varied, and the reduction of optical density, namely, the fading of latent images was scarcely observed even with a passage of time after exposure.

REFERENCE EXAMPLE

Samples 2 to 6 were produced by the same procedure as in Example 2, except that the comparative compound or the respective compounds of the present invention were added to the first layer of Sample 1 as shown in Table 3 instead of to the third layer.

The above-described samples were processed by the same procedure as in Example 2 after being preserved in a dark box at room temperature for 2 days. In Samples 3 to 6, however, the sensitivity hardly varied, the density was not reduced by the passage of time, and the fading of latent images was scarcely observed.

Further, above-described samples which were preserved at 35° C. and 80% RH for 2 weeks and ones which were preserved at room temperature for 2 weeks were exposed to blue light through an optical wedge and processed by the same procedure as in Example 2.

The results were as shown in Table 3.

TABLE 3

| Sample No. | Compound | Results of Processing after Preservation at 35° C. and 80% RH for 2 Weeks | | Results of Processing after Preservation at Room Temperature for 2 Weeks |
|---|---|---|---|---|
| | | Sensitivity (BL) | Stain | Sensitivity (BL) |
| 1 | No addition | 75 | +0.07 | 100 |
| 2 | Comparative Compound A | 95 | +0.02 | 110 |
| 3 (present invention) | Compound 19 | 97 | +0.01 | 108 |
| 4 (present invention) | Compound 11 | 95 | +0.02 | 104 |
| 5 (present invention) | Compound 20 | 96 | +0.01 | 106 |
| 6 (present invention) | Compound 6 | 97 | +0.01 | 99 |

As is understood from Table 3, the compounds of the present invention prevent the fading of latent images even with a passage of time after exposure and, also, provide the excellent preservation stability substantially equal to the comparative compound A.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a base and a silver halide emulsion layer; and a compound in an amount sufficient to prevent latent image fading represented by the formulae (1) or (II):

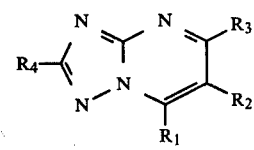  (I)

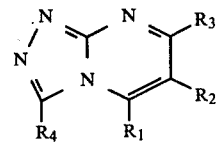  (II)

wherein $R_1$, $R_2$, and $R_3$ and $R_4$ each represents a hydrogen atom, a hydroxyl group, an alkyl group, an alkenyl group, an aralkyl group, an aryl group, an alkylthio group, an arylthio group, a mercapto group, an alkoxy group, an aryloxy group, an alkylamino group, an arylamino group, an alkoxycarbonyl group, an amino group, a halogen atom, a cyano group,

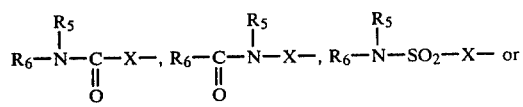

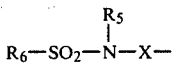

wherein X represents an alkylene divalent bonding group, and $R_5$ and $R_6$ each represents a hydrogen atom, an alkyl group, an alkenyl group, an aralkyl group, an aryl group or a heterocyclic group, in proviso that at least one of $R_1$ to $R_4$ represents a hydroxyl group and at least one of $R_1$ to $R_4$ not represented by said hydroxyl group represents

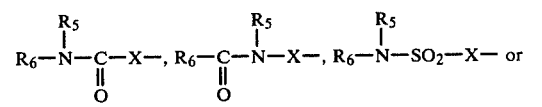

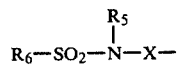

2. A silver halide photographic light-sensitive material as claimed in claim 1, wherein at least one of $R_1$ to $R_4$ is a group represented by

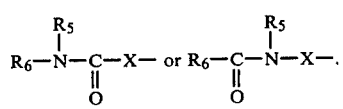

3. A silver halide photographic light-sensitive material as claimed in claim 1, wherein at least one of $R_1$ to $R_4$ is a group represented by

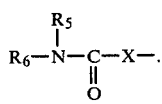

4. A silver halide photographic light-sensitive material as claimed in claim 1, wherein X represents a methylene group.

5. A silver halide photographic light-sensitive material as claimed in claim 1, wherein $R_5$ and $R_6$, which may be identical or different from each other, each represents an alkenyl group or an aralkyl group.

6. A silver halide photographic light-sensitive material as claimed in claim 1, wherein $R_5$ and $R_6$ are each an alkenyl group.

7. A silver halide photographic light-sensitive material as claimed in claim 1, wherein $R_1$ is a hydroxyl group.

8. A silver halide photographic light-sensitive material as claimed in claim 1, wherein $R_3$ is a group represented by

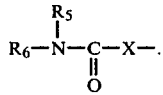

9. A silver halide photographic light-sensitive material as claimed in claim 8, wherein X represents a methylene group.

10. A silver halide photographic light-sensitive material as claimed in claim 8, wherein $R_5$ and $R_6$, which may be identical or different from each other, each represents an alkenyl group or an aralkyl group.

11. A silver halide photographic light-sensitive material as claimed in claim 8, wherein $R_5$ and $R_6$ are each an alkenyl group.

12. A silver halide photographic light-sensitive material as claimed in claim 1, wherein the compound represented by the general formulae (I) or (II) is present within the silver halide emulsion layer.

13. A silver halide photographic light-sensitive material as claimed in claim 1, wherein the compound represented by the general formulae (I) or (II) is present within a hydrophilic colloid layer present within the photographic light-sensitive material.

14. A silver halide photographic light-sensitive material as claimed in claim 1, wherein the compound represented by the general formulae (I) or (II) is present in an amount of $1 \times 10^{-5}$ to 1 mol per mol of silver halide.

15. A silver halide photographic light-sensitive material as claimed in claim 14, wherein the compound represented by the general formulae (I) or (II) is present in an amount of $2 \times 10^{-4}$ to $5 \times 10^{-2}$ mol per mol of silver halide.

* * * * *